United States Patent
Zai et al.

(10) Patent No.: US 10,435,748 B2
(45) Date of Patent: Oct. 8, 2019

(54) GENETIC MARKERS ASSOCIATED WITH SUICIDE RISK AND METHODS OF USE THEREOF

(71) Applicant: Centre for Addiction and Mental Health, Toronto (CA)

(72) Inventors: Clement C. Zai, Toronto (CA); James L. Kennedy, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 392 days.

(21) Appl. No.: 15/107,437

(22) PCT Filed: Dec. 23, 2014

(86) PCT No.: PCT/CA2014/051257
§ 371 (c)(1),
(2) Date: Jun. 22, 2016

(87) PCT Pub. No.: WO2015/095967
PCT Pub. Date: Jul. 2, 2015

(65) Prior Publication Data
US 2017/0002412 A1 Jan. 5, 2017

Related U.S. Application Data

(60) Provisional application No. 61/920,332, filed on Dec. 23, 2013.

(51) Int. Cl.
| | | |
|---|---|---|
| G06F 19/00 | (2018.01) | |
| C12Q 1/6883 | (2018.01) | |
| G16B 30/00 | (2019.01) | |
| G16H 50/30 | (2018.01) | |
| G16C 99/00 | (2019.01) | |

(52) U.S. Cl.
CPC .......... C12Q 1/6883 (2013.01); G16B 30/00 (2019.02); G16C 99/00 (2019.02); G16H 50/30 (2018.01); *C12Q 2600/156* (2013.01); *Y02A 90/26* (2018.01)

(58) Field of Classification Search
None
See application file for complete search history.

(56) References Cited

U.S. PATENT DOCUMENTS

2005/0228172 A9 10/2005 Wang
2006/0024715 A1 2/2006 Liu et al.

FOREIGN PATENT DOCUMENTS

EP 2 166 112 A1 3/2010
EP 2 166 112 B1 3/2010

OTHER PUBLICATIONS

Willour VL et al. "A Genome-Wide Association Study of Attempted Suicide", Mol Psychiatry, 17(4), 433-444; Apr. 2002 (Apr. 2002); ISSN: 1359-4184.
Scott LJ et al, "Genome-wide Association and Meta-Analysis of Bipolar Disorder in Individuals of European Ancestry", PNAS, 106(18), 7501-7506; May 5, 2009 (May 5, 2009); Online ISSN 1094-6490.
Purcell S et al, "PLINK; a Toolset for Whole-Genome Association and Population-Based Linkage Analysis." American Journal of Human Genetics, vol. 81, (2007).
Jamain S et al. "Common and Rare Variant Analysis in Early-Onset Bipolar Disorder Vulnerability", PLOS One, 9(8), e104326; Aug. 2014 (Aug. 2014); ISSN 1932-6203.
R (version 3.0.2): "The R Project for Statistical Computing", Sep. 25, 2013 (Sep. 25, 2013).
Mullins M et al, "Genetic Relationships Between Suicide Attempts, Suicidal Ideation and Major Psychiatric Disorders: A Genomic-Wide Association and Polygenic Scoring Study", American Journal of Medical Genetics Part B, 165B: 428-437; Jun. 25, 2014 (Jun. 25, 2014); Online ISSN: 1552-485X.
International Search Repot Issued in PCT/CA2014/051257 dated Mar. 16, 2015.
Anonymous (Oct. 10, 2003). Reference SNP (refSNP) Cluster Report:rs2491144, located at <https://www.ncbi.nlm.nih.gov/projects/SNP/snp_ref.cgi?rs=2491144>, last visited May 3, 2017, 2 pages.
Anonymous (Aug. 1, 2010). "BigDye Terminator v1.1 Cycle Sequencing Kit," Applied Biosystems No. Part No. 4337036, Rev. B 1, located at <https://www3.appliedbiosystems.com/cms/groups/mcb_support/documents/generaldocuments/cms_041330.pdf>last visited Apr. 4, 2011, 73 pages.

*Primary Examiner* — Anna Skibinsky
(74) *Attorney, Agent, or Firm* — Muriel Liberto, Esq.; Mintz Levin Cohn Ferris Glovsky and Popeo, P.C.

(57) ABSTRACT

Provided are polymorphic markers defined by SEQ ID Nos:1-5 which are associated with suicide risk. Also provided are methods of use of such markers as well as kits for identifying the presence of markers.

13 Claims, 1 Drawing Sheet
Specification includes a Sequence Listing.

rs2491144: (SEQ ID NO:1)

CAAGTTCCTTCTGTCTTGTTAAGCT[A/G]TTGTCATTCCGTGTTGCCCTCATTC rs9315639 (SEQ ID NO:2)

CATGCTACAGTCACCTAAAACCTGT[C/T]CTGGCTTGGATAGAATATCTTCCCA rs11082138 (SEQ ID NO:3)

GTATTTGTATTCAATCTCCACTTCA[C/T]TGGAAACTTCTTGAGGACAAATGTG rs11697517 (SEQ ID NO:4)

ATACTAAATGTTAACTTCTGCAAGT[C/T]CCTTTTCTCACTCAACATTACTGTA rs2186437 (SEQ ID NO:5)

CAGGCTGGAATGCAGTGGTGTCAAC[A/C]TATCTCCTTTTAGCCTTGAACTCCT

SEQUENCE LISTING

```
<160> NUMBER OF SEQ ID NOS: 5

<210> SEQ ID NO 1
<211> LENGTH: 52
<212> TYPE: DNA
<213> ORGANISM: Homo Sapiens

<400> SEQUENCE: 1
caagttcctt ctgtcttgtt aagctagttg tcattccgtg ttgccctcat tc          52

<210> SEQ ID NO 2
<211> LENGTH: 52
<212> TYPE: DNA
<213> ORGANISM: Homo Sapiens

<400> SEQUENCE: 2
catgctacag tcacctaaaa cctgtctctg gcttggatag aatatcttcc ca          52

<210> SEQ ID NO 3
<211> LENGTH: 52
```

```
<212> TYPE: DNA
<213> ORGANISM: Homo Sapiens

<400> SEQUENCE: 3
gtatttgtat tcaatctcca cttcacttgg aaacttcttg aggacaaatg tg            52

<210> SEQ ID NO 4
<211> LENGTH: 52
<212> TYPE: DNA
<213> ORGANISM: Homo Sapiens

<400> SEQUENCE: 4
atactaaatg ttaacttctg caagtctcct tttctcactc aacattactg ta            52

<210> SEQ ID NO 5
<211> LENGTH: 52
<212> TYPE: DNA
<213> ORGANISM: Homo Sapiens

<400> SEQUENCE: 5
caggctggaa tgcagtggtg tcaacactat ctccttttag ccttgaactc ct            52
```

GENETIC MARKERS ASSOCIATED WITH SUICIDE RISK AND METHODS OF USE THEREOF

CROSS-REFERENCES TO RELATED APPLICATIONS

This application is a national stage entry, filed under 35 U.S.C. § 371, of International Application No. PCT/CA2014/051257, filed on Dec. 23, 2014, and claims the benefit of and priority to U.S. Provisional Patent Application No. 61/920,332, filed Dec. 23, 2013, the entire contents of each of which are hereby incorporated herein by reference in their entireties and for all purposes.

INCORPORATION-BY-REFERENCE OF SEQUENCE LISTING

The content of the text file named "927000_ST25.txt", which was created on Jun. 22, 2016, and is 1.04 KB in size, is hereby incorporated by reference in its entireties and for all purposes.

FIELD OF INVENTION

The present invention relates to risk markers for suicide. More specifically, the present invention relates to genetic markers associated with suicide risk.

BACKGROUND OF THE INVENTION

Suicide claims 1 million lives each year, and for each completed suicide, there are twenty suicide attempts, making it an important public health issue. Over 90% of suicide victims have at least one psychiatric diagnosis, including bipolar disorder (Mann, 2002), where as much as 8% of bipolar patients followed for up to 40 years died from suicide (1, 2).

Suicide has a prominent genetic component (reviewed in 3). Suicide attempts tend to occur more often within families (Johnson et al, 1998; Brent et al, 2002). Greater concordance was observed between monozygotic twins than between dizygotic twins (4, 5). The concordant phenotype includes both completed and attempted suicides (4). A review of twin studies estimated the heritability of suicidal behavior to be up to 55% (6).

A number of linkage studies have been conducted on suicide (7, 8). Their findings on the short arm of chromosome 2 were later replicated in 162 bipolar disorder families (9). Recent technological advances have permitted the high-throughput genotyping of hundreds of thousands of single-nucleotide polymorphisms across the genome. A number of suggestive findings have emerged (10, 11). Recently, a genome-wide association study (GWAS) was reported on samples of 2698 bipolar disorder patients of which 1201 had a previous suicide attempt. After meta-analysis of markers with $p<1\times10^{-3}$ from their discovery sample (GAIN, TGEN, German) with their replication bipolar disorder sample (STEP-BD, WTCCC, UCL), the most significantly associated marker was rs300774 in an intergenic region at chromosomal region 2p25, which contains the SH3YL1, ACP1, and FAM150B genes. The association finding was supported by post-mortem prefrontal cortical gene expression analysis, where suicide completers were found to have significantly higher ACP1 expression than non-suicide victims (12). The strongest association signal from another GWAS of suicide attempt on the bipolar disorder (STEP-BD, WTCCC, UCL) came from the intergenic chromosome 10 marker rs1466846; this finding was not replicated in the replication sample (GAIN, TGEN, German) (10). A GWAS on suicidality scores, which are derived from the SCAN interview, was conducted with a major depression sample from the RADIANT study (11). The suicidality score captures suicide severity from suicide ideation to attempt. The most significant findings from the RADIANT sample failed to replicate in the German replication sample.

At the present time, there is a lack of meaningful genetic predictors of suicidal behavior. Thus, there is a need in the art for diagnostic assays and tests to identify subjects at risk for suicide. Further there is a need in the art to genetic markers and kits that can be used to identify subjects at risk for suicide.

SUMMARY OF THE INVENTION

The present invention relates to risk markers for suicide. More specifically, the present invention relates to genetic risk markers for suicide and use thereof.

According to the present invention, there is provided a method of identifying a subject at risk for suicide comprising identifying in a biological sample from the subject one or more genetic markers associated with suicide, at least one marker being defined by rs2491144 (SEQ ID NO:1), wherein the presence of the G allele in marker rs2491144 identifies the subject is at increased risk for suicide.

According to the present invention, there is provided a method as described above and herein further comprising identifying one or more additional genetic markers associated with suicide in the biological sample from the subject, the one or more additional genetic markers being defined by the group consisting of rs9315639 (SEQ ID NO:2), rs11082138 (SEQ ID NO:3), rs11697517 (SEQ ID NO:4), and rs2186437 (SEQ ID NO:5), wherein the presence of any of the C allele in marker rs9315639, the C allele in marker rs11082138, the T allele in marker rs11697517, and C allele in marker rs2186437 identifies the subject is at increased risk for suicide.

According to the present invention, there is also provided a method as described above and herein, further comprising a step of obtaining the biological sample from the subject.

According to the present invention, there is also provided a method as described above and herein wherein the biological sample is a sample from blood, saliva, spinal fluid, brain biopsy, cultured cells obtained from the subject, stool, urine, autopsy samples, or frozen sections taken for histological purposes.

According to the present invention, there is also provided a method as described above and herein wherein the step of identifying in a biological sample from the subject one or more genetic markers associated with suicide comprises PCR analysis, sequencing, 5'exonuclease fluorescence assay, probe hybridization or a combination thereof.

According to the present invention, there is also provided a method as described above and herein wherein the subject is a subject diagnosed with a mental illness.

According to the present invention there is also provided a method as described above and herein wherein the mental illness is selected from the group consisting of depression, schizophrenia, schizoaffective disorder, bipolar disorder, personality disorder, seasonal affective disorder, anxiety disorder, and post traumatic stress disorder.

According to the present invention there is also provided a method as described above and herein wherein the subject exhibits one or more clinical symptoms of a mental illness.

According to the present invention there is also provided a method as described above and herein wherein the subject exhibits one or more symptoms of a mental illness selected from the group consisting of depression, schizophrenia, schizoaffective disorder, bipolar disorder, personality disorder, seasonal affective disorder, anxiety disorder, and post traumatic stress disorder.

According to the present invention there is also provided a method as described above and herein further comprising receiving, in a computer system, the subject's genotype for the one or more genetic markers associated with suicide and the identifying step is performed by the computer system.

According to the present invention there is also provided a method as described above and herein wherein the subject's genotype is received directly from equipment used in determining the patient's genotype.

According to the present invention there is also provided a method as described above and herein further comprising receiving, in a computer system, the patient's diagnosis.

According to the present invention there is also provided a method as described above and herein further comprising a step of outputting an indication of whether or not the subject is at increased risk for suicide.

According to the present invention there is also provided a method as described above and herein wherein the indication of whether or not the subject is at increased risk for suicide is represented on a patient specific report.

According to the present invention there is also provided a computer readable medium containing executable instructions that when executed cause one or a plurality of processors to receive a subject's genotype for one or more genetic markers associated with suicide selected from the group consisting of rs2491144 (SEQ ID NO:1), rs9315639 (SEQ ID NO:2), rs11082138 (SEQ ID NO:3), rs11697517 (SEQ ID NO:4), and rs2186437 (SEQ ID NO:5); identify the presence of any of the G allele in marker rs2491144 (SEQ ID NO:1), the C allele in marker rs9315639 (SEQ ID NO:2), the C allele in marker rs11082138 (SEQ ID NO:3), the T allele in marker rs11697517 (SEQ ID NO:4), and C allele in marker rs2186437 (SEQ ID NO:5), and output an indication that the subject is at increased risk for suicide if at least the G allele in marker rs2491144 (SEQ ID NO:1) is present or a null result if the G allele in marker rs2491144 (SEQ ID NO:1) is absent.

According to the present invention, there is also provided a method for reducing the risk of suicide in a subject identified as being at increased risk for suicide according to the method as described above and herein, the method comprising one or more of
a) treating the subject with medication, non-medicinal therapy or a combination thereof;
b) monitoring the subject;
c) counseling the subject;
d) testing or screening the subject for mental illness or one or more symptoms that are associated with mental illness or suicide,
e) testing the biological sample comprising genomic DNA or a second biological sample obtained from the subject for one or more additional genetic markers, nucleotide sequences, proteins, metabolites or any combination thereof;
f) removing or reducing access to compounds, compositions, articles or cues which increase suicide risk, or any combination thereof.

According to the present invention there is also provided a method as described above and herein wherein treating the subject with medication comprises administering one or more antipsychotics, mood stabilizers, antidepressants, anticonvulsants, antianxiolytics, or any combination thereof.

According to the present invention there is also provided a method as described above and herein wherein the medication comprises clozapine, lithium, or ketamine.

According to the present invention there is also provided a method as described above and herein wherein the non-medicinal therapy comprises electroconvulsive or electroshock therapy, magnetic seizure therapy, transcranial magnetic stimulation, cognitive behavioral therapy, dialectical behavioral therapy, risk dissipation group therapy, deep brain stimulation, or a combination thereof.

According to the present invention there is also provided a method as described above and herein wherein said testing or screening the subject for mental illness or one or more symptoms associated with suicide or mental illness comprises testing or screening the subject for depression, schizophrenia, schizoaffective disorder, bipolar disorder, obsessive compulsive disorder, personality disorder, seasonal affective disorder, addiction, drug abuse, alcoholism, problem gambling, increased anxiety, anxiety disorder, feelings of worthlessness, psychotic symptoms, delusions, hallucinations, agitation, restlessness, irritability, aggression or anger.

According to the present invention there is also provided a kit comprising,
a) one or more primers to amplify a nucleotide sequence that comprises the polymorphism as defined in:
rs2491144 (SEQ ID NO:1) or a fragment thereof comprising the polymorphic site, or the complement of SEQ ID NO:1 or a fragment thereof comprising the polymorphic site;
rs9315639 (SEQ ID NO:2) or a fragment thereof comprising the polymorphic site, or the complement of SEQ ID NO:2 or a fragment thereof comprising the polymorphic site,
rs11082138 (SEQ ID NO:3) or a fragment thereof comprising the polymorphic site, or the complement of SEQ ID NO:3 or a fragment thereof comprising the polymorphic site,
rs11697517 (SEQ ID NO:4) or a fragment thereof comprising the polymorphic site, or the complement of SEQ ID NO:4 or a fragment thereof comprising the polymorphic site,
rs2186437 (SEQ ID NO:5) or a fragment thereof comprising the polymorphic site, or the complement of SEQ ID NO:5 or a fragment thereof comprising the polymorphic site,
or any combination thereof;
b) one or more probes that hybridize to SEQ ID NOs:1, 2, 3, 4, or 5, or the complement thereof, over a region of nucleotides comprising the polymorphic site, wherein said probe hybridizes to a particular variant of the polymorphism at the polymorphic site;
c) one or more reagents and/or products comprising buffers, nucleotides, DNA amplifying enzymes, or any combination thereof;
d) one or more reagents, components and/or products for genotyping the polymorphisms of SEQ ID NO:1, 2, 3, 4, 5, their complements or any combination thereof,
e) one or more reagents, components and/or products for performing a DNA sequencing reaction that determines the sequence of SEQ ID NO: 1, 2, 3, 4, 5, their complements or any combination thereof,
f) a gene chip or nucleotide sequence array comprising a plurality of nucleotide sequences comprising or consisting of any one or combination of SEQ ID NOs:1-5, a fragment thereof comprising the polymorphic site or their complements;

g) one or more instructions for using the components as described herein, practicing the methods as described herein, interpreting the data obtained from practicing the methods, or any combination thereof;
h) a scale, reference or the like that may be used to test, diagnose, monitor or determine symptoms of the subject; or any combination or sub-combination of a) through h).

According to the present invention there is also provided a kit as defined above and herein comprising,
a) one or more primers to amplify a nucleotide sequence that comprises the polymorphism as defined in rs2491144 (SEQ ID NO:1), rs9315639 (SEQ ID NO:2), rs11082138 (SEQ ID NO:3), rs11697517 (SEQ ID NO:4), rs2186437 (SEQ ID NO:5) or any combination thereof;
b) one or more probes that hybridize to SEQ ID NOs:1, 2, 3, 4, or 5, over a region of nucleotides comprising the polymorphic site, wherein said probe hybridizes to a particular variant of the polymorphism at the polymorphic site.
c) one or more reagents and/or products comprising buffers, nucleotides, DNA amplifying enzymes, or any combination thereof;
d) one or more reagents, components and/or products for genotyping the polymorphisms of SEQ ID NO:1, 2, 3, 4, 5, or a combination thereof,
e) one or more reagents, components and/or products for performing a DNA sequencing reaction that determines the sequence of SEQ ID NO: 1, 2, 3, 4, 5, or a combination thereof,
f) a gene chip or nucleotide sequence array comprising a plurality of nucleotide sequences comprising or consisting of SEQ ID NOs:1-5, and;
g) one or more instructions for using the components as described herein, practicing the methods as described herein, interpreting the data obtained from practicing the methods, or any combination thereof;
h) a scale, reference or the like that may be used to test, diagnose, monitor or determine symptoms of the a subject; or any combination or sub-combination of a) through h).

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows the nucleotide sequences of rs2491144 (SEQ ID NO:1), rs9315639 (SEQ ID NO:2), rs11082138 (SEQ ID NO:3), rs11697517 (SEQ ID NO:4) and rs2186437 (SEQ ID NO:5). The polymorphic site is shown underlined in square brackets.

DETAILED DESCRIPTION

The following description is of a preferred embodiment.

The present invention provides a method of identifying a subject that is at risk for suicide comprising,
testing a biological sample comprising genomic DNA of the subject to determine if the genomic DNA comprises one or more polymorphic markers associated with suicide defined by 1) rs2491144 (SEQ ID NO:1) or a fragment thereof comprising the polymorphic site, or a nucleotide sequence which is the complement of SEQ ID NO:1 or the fragment thereof comprising the polymorphic site; 2) rs9315639 (SEQ ID NO:2) or a fragment thereof comprising the polymorphic site, or a nucleotide sequence which is the complement of rs9315639 (SEQ ID NO:2) or a fragment thereof comprising the polymorphic site; 3) rs11082138 (SEQ ID NO:3) or a fragment thereof comprising the polymorphic site, or a nucleotide sequence which is the complement of rs11082138 (SEQ ID NO:3) or a fragment thereof comprising the polymorphic site; rs11697517 (SEQ ID NO:4) or a fragment thereof comprising the polymorphic site, or a nucleotide sequence which is the complement of rs11697517 (SEQ ID NO:4) or a fragment thereof comprising the polymorphic site; rs2186437 (SEQ ID NO:5) or a fragment thereof comprising the polymorphic site, or a nucleotide sequence which is the complement of rs2186437 (SEQ ID NO:5) or a fragment thereof comprising the polymorphic site, wherein the presence of the G allele in marker rs2491144 identifies the subject is at increased risk for suicide, the presence of the C allele in marker rs9315639 identifies the subject is at increased risk for suicide, the presence of the C allele in marker rs11082138 identifies the subject is at increased risk for suicide, the presence of the T allele in marker rs11697517 identifies the subject is at increased risk for suicide, and; the presence of the C allele in marker rs2186437 identifies the subject is at increased risk for suicide.

Preferably the fragments of the markers are at least 7 consecutive nucleotides, for example 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of the markers described in SEQ ID NO:1-5 or the complement thereof.

The present invention also provides a method of identifying a subject that is at risk for suicide comprising, testing a biological sample comprising genomic DNA of the subject to determine if the genomic DNA comprises one or more polymorphic markers associated with suicide defined by rs2491144 (SEQ ID NO:1), rs9315639 (SEQ ID NO:2), rs11082138 (SEQ ID NO:3), rs11697517 (SEQ ID NO:4), rs2186437 (SEQ ID NO:5) or a combination thereof, wherein the presence of the G allele in marker rs2491144 identifies the subject is at increased risk for suicide, the presence of the C allele in marker rs9315639 identifies the subject is at increased risk for suicide, the presence of the C allele in marker rs11082138 identifies the subject is at increased risk for suicide, the presence of the T allele in marker rs11697517 identifies the subject is at increased risk for suicide, and; the presence of the C allele in marker rs2186437 identifies the subject is at increased risk for suicide.

In a preferred embodiment, the marker is rs2491144. In a further embodiment the one or more markers is rs2491144 and at least one of rs9315639, rs11082138, rs11697517, and rs2186437. In still a further embodiment, the marker is rs2491144 and this marker is employed in combination with one or more additional genetic markers that are known in the art to be predictive of suicide risk and/or mental illness.

In a further embodiment of the present invention, the method may be practiced as described above, but the testing a biological sample comprises testing the biological sample for genomic DNA of the subject to determine if the genomic DNA comprises one or more markers comprising the polymorphism that exhibits between 90% and 100% sequence identity to the markers described, for example, but not limited to, 90%, 91%, 92%, 93%, 94%, 95%, 96%, 97%, 98%, 99%, 99.5%, 99.9% or 100% sequence identity with SEQ ID NO:1, SEQ ID NO:2, SEQ ID NO:3, SEQ ID NO:4, or SEQ ID: NO:5, or a fragment thereof and wherein the sequence also comprises the respective polymorphisms as shown above in underlined brackets. As will be understood by a person of skill in the art, it is also possible to determine sequences which exhibit the sequence identity range noted above for the complement of the sequences described. As an example, but not to be considered limiting in any manner, the first nucleotide shown in SEQ ID NO:1 is a "C". The present invention is meant to include a sequence that is substantially identical to SEQ ID NO:1 but that comprises a different nucleotide, for example, a "G" at position number 1, as the variant nucleotide sequence exhibits more than 90% sequence identity with SEQ ID NO:1 and comprises the polymorphism shown in underlined brackets.

To determine whether a nucleic acid or DNA exhibits similarity or a percentage identity with the sequences presented herein, oligonucleotide alignment algorithms may be used, for example, but not limited to a BLAST (GenBank URL: www.ncbi.nlm.nih.gov/cgi-bin/BLAST/, using default parameters: Program: blastn; Database: nr; Expect 10; filter: default; Alignment: pairwise; Query genetic Codes: Standard(1)), BLAST2 (EMBL URL: http://www.embl-heidelberg.de/Services/index.html using default parameters: Matrix BLOSUM62; Filter: default, echofilter: on, Expect:10, cutoff: default; Strand: both; Descriptions: 50, Alignments: 50), or FASTA, search, using default parameters. Polypeptide alignment algorithms are also available, for example, without limitation, BLAST 2 Sequences (www.ncbi.nlm.nih.gov/blast/bl2seq/bl2.html, using default parameters Program: blastp; Matrix: BLOSUM62; Open gap (11) and extension gap (1) penalties; gap x_dropoff: 50; Expect 10; Word size: 3; filter: default).

An alternative indication that two nucleic acid sequences are substantially identical is that the two sequences hybridize to each other under moderately stringent, or preferably stringent conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/ 0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. for at least 1 hour. Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, but not wishing to be limiting, stringent conditions are selected to be about 5° C. lower than the thermal melting point for the specific sequence at a defined ionic strength and pH.

In an embodiment of the present invention, but without wishing to be limiting in any manner, the method as described herein may be employed to identify, treat or treat preventatively a subject that is at risk for suicide wherein at the time of testing or screening the subject appears healthy. This information may be important when testing/screening subjects that have a familial history of suicide or suicide attempts or mental illness, for example, but not limited to bipolar disease, schizophrenia or another mental illness, even though at the time of testing/screening, the subject may have little or no symptoms of disease or has not exhibited symptoms associated with suicide. Knowledge that the subject has one or more genetic markers associated with a higher risk of suicide may be useful in many ways, for example, by implementing proactive measures to reduce suicide risk at the earliest time possible or developing treatment regimens if for example, the subject later develops a mental illness such as, without limitation, bipolar disease, schizophrenia or another mental illness and requires treatment.

The present invention also contemplates a method as described above that further comprises one or more steps to reduce the subject's risk of suicide. Such steps may comprise, but are not limited to treating the subject with medication such as, for example one or more antipsychotics, including typical and atypical antipsychotics, mood stabilizers, antidepressants, anticonvulsants, or other type(s) of medication, for example, but not wishing to be limiting, lithium, clozapine or ketamine.

By the term "antipsychotics" or "antipsychotic medication" it is meant any drug, pharmaceutical, natural product, composition or the like that may be employed to prevent and/or treat psychosis, schizophrenia, schizoaffective disorder, disruptive behavior, disorganized thinking, symptoms of mania, or any combination thereof in a subject. Antipsychotic medication may comprise, but is not limited to, drugs that affect dopamine signaling, for example, drugs that bind reversibly or irreversibly to one or more dopamine receptors, drugs that act as competitive or non-competitive inhibitors to downregulate dopamine receptor signaling, or that block the dopamine D2 receptor (see for example Seeman et al, 1976 and Seeman et al, 2005). Without wishing to be limiting, antipsychotic drugs comprise clozapine, olanzapine, trifluoperazine, thioridazine, haloperidol, haloperidol decanoate, thiothixene, chlorpromazine, fluphenazine, loxapine, perphenazine, perphenazine decanoate, perphenazine-amitriptyline, acetophenazine, molindone, mesoridazine, fluphenazine decanoate, methotrimeprazine, risperidone, aripiprazole or a combination thereof. In a preferred embodiment, the antipsychotic drug comprises clozapine or a combination therapy comprising clozapine.

The subject may also be treated with one or more non-medicinal therapies alone or in combination with treatment with medication. Such non-medicinal therapies include, but are not limited to electroconvulsive therapy or electroshock therapy, transcranial magnetic stimulation, cognitive behavioral therapy, dialectical behavioral therapy, risk dissipation group therapy or a combination thereof.

It is also contemplated that the subject may be subjected to monitoring, for example more frequent or intensive monitoring by a physician, clinician, health care provider or family member. Alternatively, or in combination therewith, the subject may be subjected to counseling by a physician, psychologist, health care provider or the like.

The method also contemplates embodiments wherein the subject is further tested or screened for one or more mental illnesses or one or more symptoms that are associated with mental illness or suicide. Such mental illnesses may include, but are not limited to depression, schizophrenia, schizoaffective disorder, bipolar disorder, obsessive compulsive disorder, personality disorder, seasonal affective disorder, mood disorder, post traumatic stress disorder, addiction, drug abuse, alcoholism, problem gambling and the like. Symptoms that are associated with mental illness are well known in the art and may be obtained from psychiatric diagnostic manuals known in the art, for example the Diagnostic and Statistical Manual of Mental Disorders (DSM IV) and the like. Symptoms that can be associated with suicide include, among others, increased anxiety, feelings of worthlessness, psychotic symptoms, delusions, hallucinations, agitation, restlessness, irritability, aggression or anger.

As described above, but without wishing to be limiting in any manner, the subject that is tested may comprise an individual that has been diagnosed with a mental illness or exhibits one or more symptoms of a mental illness such as, without limitation, depression, bipolar symptoms, psychotic symptoms, schizophrenia symptoms, schizoaffective disorder symptoms or a combination thereof, for example, but not limited to as described in DSM-IV which is hereby incorporated by reference. Psychotic symptoms may comprise positive symptoms such as, but not limited to distortions or exaggerations of inferential thinking (i.e. delusions), perception (i.e. hallucinations), language and communication (disorganised speech) and behavior (grossly disorganized or catatonic behavior) or any combination thereof. Further, the positive symptoms may comprise distinct dimensions, for example, psychotic dimensions including, but not limited to delusions and hallucinations and disorganization dimensions including, but not limited to disorganized speech and behavior. As described previously, it is also contemplated that the symptoms may comprise one or more negative symptoms, for example, but not limited to symptoms that reflect a diminution or loss of normal function. Further, the subject may exhibit a combination of both positive and negative symptoms. In a preferred embodiment of the invention, the subject that is tested has been diagnosed or is suspected of having bipolar disorder, schizophrenia or schizoaffective disorder.

The method described above also contemplates testing the biological sample comprising DNA or a second biological sample obtained from the subject for one or more additional genetic markers, nucleotide sequences, proteins, metabolites or any combination thereof. For example, but without wishing to be limiting in any manner, the same or a different biological sample from the subject may be tested for other genetic markers known in the art that are associated with suicide ideation or mental illness including, but not limited to bipolar disease, schizophrenia, schizoaffective disorder and the like. The subject also may be tested for markers that predict drug treatment outcome or that assist in determining drug treatment. Similarly, the subject may be tested to determine the presence of alcohol or drugs in blood or to determine the level of alcohol or drugs in blood, as it is known that alcohol and drug use may be contributing factors to suicidal tendencies and may also interact with drug treatment regimens.

The method as described herein also contemplates removing or reducing access to compounds, compositions, articles or cues such as alcohol, drugs and the like which may increase suicide risk.

Also provided by the present invention is a method wherein the subject is diagnosed with a mental illness or exhibits one or more symptoms of a mental illness prior to testing the biological sample. For example, the present invention provides:
A method of identifying a subject who is diagnosed with a mental illness or who exhibits one or more symptoms of a mental illness for suicide risk comprising,
testing a biological sample comprising genomic DNA of the subject to determine if the genomic DNA comprises one or more markers defined by rs2491144 (SEQ ID NO:1), rs9315639 (SEQ ID NO:2), rs11082138 (SEQ ID NO:3), rs11697517 (SEQ ID NO:4), rs2186437 (SEQ ID NO:5) or a combination thereof, wherein the presence of the G allele in marker rs2491144 identifies the subject is at increased risk for suicide,
the presence of the C allele in marker rs9315639 identifies the subject is at increased risk for suicide,
the presence of the C allele in marker rs11082138 identifies the subject is at increased risk for suicide,
the presence of the T allele in marker rs11697517 identifies the subject is at increased risk for suicide, and;
the presence of the C allele in marker rs2186437 identifies the subject is at increased risk for suicide.

Thus, according to the present invention, the method as described herein may further comprise selecting a subject that is diagnosed with a mental illness or that exhibits one or more symptoms associated with suicide or mental illness and obtaining the biological sample from the subject.

Any tissue sample may be used for genotyping the polymorphisms in SEQ ID NO:1-5, including but not limited to, blood, saliva, spinal fluid, brain biopsy, cultured cells obtained from the subject, stool, urine, autopsy samples, or frozen sections taken for histological purposes. In a preferred embodiment blood is obtained from a subject for assaying with respect to above mentioned polymorphisms. As an example, but without wishing to be limiting in any manner, venous blood is obtained from a subject using standard venipuncture techniques.

Polymorphisms may be genotyped using conventional techniques. For example, PCR using primers incorporating fluorescent probes is one suitable technique. Further, but not wishing to be considered limiting, primers having appropriate sequences upstream and downstream of the polymorphic site may be used to amplify the nucleotide regions comprising the polymorphisms.

Single nucleotide polymorphism (SNP) analysis is useful for detecting differences between alleles of a gene or nucleotide sequence. As described above, various methods exist in the art for genotyping nucleotide sequences including, but not limited to 5'exonuclease assays, nucleotide sequencing, probe hybridization and the like. All such methods are meant to be encompassed herein. Further, various real-time PCR methods that can be used to detect SNPs, including, e.g., Taqman or molecular beacon-based assays (U.S. Pat. Nos. 5,210,015; 5,487,972; and PCT WO 95/13399) are useful to monitor for the presence or absence of a SNP. Still other SNP detection methods are known in the art, including, without limitation, DNA sequencing, sequencing by hybridization, dot blotting, and oligonucleotide array (DNA Chip) hybridization analysis.

Applied Biosystems, Inc (Foster City, Calif.) has developed several aspects of SNP genotyping technology. In one well-used protocol, PCR amplification of a desired SNP region is conducted using targeting primers, including two allele-specific fluorogenic probes, each consisting of a different fluorescent reporter dye and a fluorescent quencher. Prior to PCR, proximity of the quencher to the fluorophore causes fluorescence resonance energy transfer (FRET), reducing the fluorescence from the reporter dye. During PCR, the 5' nuclease activity of Taq digests the allele-specific probe bound to the region of the SNP, releasing the fluorescent dye from the quencher and allowing generation of a fluorescence signal.

In a preferred embodiment, the presence of a particular allele at the polymorphic site, for example, as provided by SEQ ID NOs: 1-5 is determined in relation to the adjacent nucleotide sequence upstream and downstream from the polymorphic site, for example, but not limited to, about 3, 4, 5, 6, 7, 8, 9, 10, 11, 12, 13, 14 or 15 nucleotides upstream and/or about 3, 4, 5, 6, 7, 8, 9, 10, 11, 12, 13, 14 or 15 nucleotides downstream of the polymorphic site. However, the present invention also contemplates that the presence of a particular allele may be determined in relation to the nucleotide sequence comprising about 20, 25, 30, 50 or more nucleotides upstream (or any number therein between) and about 20, 25, 30, 50 and/or more nucleotides downstream (or any number therein between) of the polymorphic site as provided by SEQ ID NOs: 1-5, respectively. The term "and/or" is used to specifically indicate that the number of continuous upstream and downstream nucleotides does not need to be the same. Other means and methods of comparing nucleotide sequences to determine if a particular polymorphism or group of polymorphisms is present in a subject, as would be known to a person of skill in the art may be employed in the practice of the present invention.

The method of obtaining a sample and analyzing its nucleotide sequence or DNA is not critical to the present invention and any methods may be used (e.g. Ausubel, et al. (eds), 1989, Current Protocols in Molecular Biology, Green Publishing Associates, Inc., and John Wiley & Sons, Inc., New York, at p. 2.10.3, or Maniatis et al., in Molecular Cloning (A Laboratory Manual), Cold Spring Harbor Laboratory, 1982, p. 387 389). For example, which is not to be considered limiting in any manner, DNA may be extracted using a non-enzymatic high-salt procedure. Alternatively, the DNA may be analyzed in situ. Other methods of DNA analysis that are known to persons skilled in the art may also be used. For nucleotide sequences that reside within exons of gene sequences and are expressed, the RNAs that are produced may be isolated and analyzed by well-known methods known in the art and is meant to be encompassed by the method of the present invention as described herein.

Also provided by the present invention is a kit comprising, a) one or more primers to amplify a nucleotide sequence that comprises the polymorphism as defined in rs2491144 (SEQ ID NO:1) or a fragment thereof which comprises the polymorphic site; rs9315639 (SEQ ID NO:2) or a fragment thereof which comprises the polymorphic site; rs11082138 (SEQ ID NO:3) or a fragment thereof which comprises the polymorphic site; rs11697517 (SEQ ID NO:4) or a fragment thereof which comprises the polymorphic site; rs2186437 (SEQ ID NO:5) or a fragment thereof which comprises the polymorphic site or any combination thereof. As will be understood by a person of a person of skill of the art, primers comprising or consisting of the nucleotide sequence which is the complement of those described above may also be used, as are sequences which exhibit about 90-100% sequence identity, for example, but not limited to 90%, 91%, 92%, 93%, 94%, 95%, 96%, 97%, 98%, 99%, 99.5%, 99.9% or 100% to those described above or a sequence that is complementary thereto;

b) one or more probes that hybridize to SEQ ID NOs:1, 2, 3, 4, 5, a fragment thereof comprising the polymorphic site or their complementary sequence over a region of nucleotides comprising the polymorphic site, wherein said probe hybridizes to a particular variant of the polymorphism at the polymorphic site. Also, without wishing to be limiting in any manner, the probes may be labeled with an appropriate group, for example, a fluorescent tag, fluorophore, radioactive label or the like. Further, the one or more probes may be attached covalently or physically associated with a support for example, but not limited to a bio-chip, array, slide, multiwell plate, bead or the like. In an embodiment, which is not meant to be limiting in any manner, the probes may comprise an array of nucleic acids;

c) one or more reagents and/or products comprising buffers, nucleotides, DNA amplifying enzymes, or any combination thereof;

d) one or more reagents, components and/or products for genotyping the polymorphisms of SEQ ID NO:1, 2, 3, 4, 5, or a combination thereof, e) one or more reagents, components and/or products for performing a DNA sequencing reaction that determines the sequence of SEQ ID NO: 1, 2, 3, 4, 5, or a combination thereof, f) a gene chip or nucleotide sequence array comprising one or more nucleotide sequences comprising or consisting of SEQ ID NOs:1-5, a fragment thereof or their complement;

g) one or more instructions for using the components as described herein, practicing the methods as described herein, interpreting the data obtained from practicing the methods, or any combination thereof;

h) a scale, reference or the like that may be used to test, diagnose, monitor or determine symptoms of the subject; or any combination or sub-combination of a) through h).

As will be understood by a person of skill in the art, the subject matter herein may be practiced as recited or it may be practiced by employing/determining/analyzing the complement of the nucleotide sequences recited herein.

The present invention will be further illustrated in the following examples.

EXAMPLES

Methods

We recruited a sample of 334 bipolar disorder patients (Sample GBP) at the Centre for Addiction and Mental Health in Toronto, Canada. Details on the GBP sample have been described previously (13). The participants were at least 18 years of age at time of enrolment and reported European ancestry through self-report. They were recruited through advertisements in family doctors' offices, clinics, hospitals, and patient support groups. Their diagnoses for bipolar disorder according to DSM-IV and ICD-10 criteria were confirmed using the Schedules for Clinical Assessment in Neuropsychiatry (SCAN). Exclusion criteria included a diagnosis of intravenous drug dependency, reported intravenous drug use, the presence of mood incongruent psychotic symptoms, manic episodes only in conjunction with or as a result of alcohol, substance abuse, substance dependence, medical illnesses, or medication.

Genotyping. Sample GBP was genotyped with the Illumina Sentrix Human Hap550 Beadchip (Illumina Inc., San Diego, Calif., USA) mostly at Illumina Inc. (San Diego, Calif., USA), with 290 subjects being genotyped at the Genome Quebec facility (Montreal, Quebec, Canada).

Quality Control & Statistical Analysis. We applied the same quality control measures using PLINK (14) and R (R Development Core Team (2008). R: A language and environment for statistical computing. R Foundation for Statistical Computing, Vienna, Austria. ISBN 3-900051-07-0, URL http://www.R-project.org.). Briefly, individuals with less than 95% of the markers genotyped were removed, and markers with less than 95% genotyped or with minor allele frequency of less than 5% were excluded. Cryptic relatedness were assessed and one individual of each pair of related individuals (PI_HAT>0.05) was removed based on the amount of missing phenotype or genotype information. Mean heterozygosity was determined, and individuals lying outside of four standard deviations from this mean were removed. Markers of which genotypes deviated significantly from Hardy-Weinberg Equilibrium (p<0.001) were excluded from subsequent analyses. We ran a multi-dimensional scaling (MDS) analysis of the genotypes by multidimensional scaling to ascertain the ethnicity of the samples, and we removed the discrete cluster that corresponded to the self-reported Jewish ancestry (of all four grandparents). After sample refinement and updating map position to b37, we have 438,625 markers for 308 GBP cases. We conducted whole-genome imputation using IMPUTE2 (15) in 5-Mb segments after prephasing in SHAPEIT2 (16) for all three samples with 1000 Genome Project (17) b37 genotypes as reference. Then we converted the format to PLINK using GTOOL (Genetics Software Suite, © 2007, The University of Oxford) with a genotype call threshold of 0.9. Then, we performed linear regression on suicide severity for the GBP sample in PLINK. We included age, sex, past alcohol use disorder, the number of depressive episodes; and the first four components from the MDS analysis as covariates.

We found rs2491144 on chromosome 1 to be associated with suicide severity in the GBP sample (p<0.05; Table 1). We also found positive findings in the GBP sample with a number of other markers: rs9315639 on chromosome 13, rs11082138 on chromosome 18, and rs11697517 on chromosome 20, and rs2186437 on chromosome 21.

TABLE 1

Summary of findings from the genetic analysis of suicide severity scores in our GBP bipolar disorder sample. BETA indicating the direction of marker effect is included.

| | | | | GBP | |
|---|---|---|---|---|---|
| CHR | BP | SNP | A1 | BETA | P |
| 1 | 31327011 | rs2491144 | A | −0.03176 | 0.01044 |
| 13 | 39544663 | rs9315639 | T | −0.02641 | 0.02058 |
| 18 | 36998210 | rs11082138 | C | 0.04379 | 0.01791 |
| 20 | 48409772 | rs11697517 | T | 0.03377 | 0.003861 |
| 21 | 25870353 | rs2186437 | A | −0.04142 | 0.008687 |

The results in Table 1 indicate:
For rs2491144, because the BETA is negative, with each additional copy of the test allele (A), there is a decreased risk for higher suicide severity compared to the G allele. Thus GG is a higher risk genotype.
For rs9315639, because the BETA is negative, with each additional copy of the test allele (T), there is a decreased risk for higher suicide severity scores compared to the C allele. Thus CC is a higher risk genotype.
For rs11082138, because the BETA is positive, with each additional copy of the test allele (C), there is an increased risk for higher suicide severity scores compared to the T allele. Thus CC is a higher risk genotype.
For rs11697517, because the BETA is positive, with each additional copy of the test allele (T), there is an increased risk for higher suicide severity scores compared to the C allele. Thus TT is a higher risk genotype.
For rs2186437, because the BETA is negative, with each additional copy of the test allele (A), there is a decreased risk for higher suicide severity scores compared to the C allele. Thus CC is a higher risk genotype.

One interesting marker that was tested (rs2491144) is mapped to the 3' region of SDC3 coding for the syndecan 3 protein, which is highly expressed in neural cells (18), and may be important in brain development (19). Studies on mice deficient in sdc3 indicated a role of this protein in long-term potentiation and hippocampal memory (20). The rs9315639 marker is mapped to the STOML3 stomatin (EPB72)-like 3 gene, which appears to be important for mechanoreceptor mediated signal transduction in sensory neurons (21). The rs2186437 marker is located approximately 1.4 Mb 3' of the amyloid beta (A4) precursor protein-coding gene APP, which has been implicated in Alzheimer's disease.

The rs11082138 marker resides in a non-protein-coding RNA gene called LINC00669 (uncharacterized LOC647946), within which lies three microRNA genes, MIR5583-5p, MIR5583-3p, and MIR924. Of the predicted targets for MIR5583-5p, the NR3C1 gene (DIANA Lab: rank #8 with miTG Score=0.9828; mirDB: rank #25 with Target Score=87) codes for the glucocorticoid receptor. The promoter methylation of NR3C1 was shown to be modified by childhood trauma (22, 23). Of the predicted targets for MIR5583-3p, the NR3C2 gene (DIANA Lab: rank #5 with miTG Score=0.9872; mirDB: rank #17 with Target Score=86) codes for the mineralocorticoid receptor, the ADRB1 gene (DIANA Lab: rank #24 with miTG Score=0.9542; mirDB: rank #35 with Target Score=80) codes for the beta 1 adrenoceptor, the PGR gene (DIANA Lab: rank #38 with miTG Score=0.9382; mirDB: rank #2 with Target Score=98) codes for the progesterone receptor, which interacts with FKBP5 (24) and regulate FKBP5 expression (25), and the FMR1 gene (DIANA Lab: rank #3 with miTG Score=0.9909; mirDB: rank #21 with Target Score=83) encodes the Fragile X Mental Retardation 1 protein in which expansion of the (CGG)n trinucleotide repeat in the 5' untranslated region causes Fragile X Syndrome. Markers in FMR1 have recently been associated with depressed mood in sleep disorder patients (26), and FMR1 premutation has been associated with altered hypothalamic-pituitary-adrenal axis activity (27).

REFERENCES

1. Angst F, Stassen H H, Clayton P J, Angst J. Mortality of patients with mood disorders: follow-up over 34-38 years. J Affect Disord 2002; 68(2-3): 167-181.
2. Nordentoft M, Mortensen P B, Pedersen C B. Absolute risk of suicide after first hospital contact in mental disorder. Arch Gen Psychiatry 2011; 68(10): 1058-1064.
3. Zai C C, de Luca V, Strauss J, Tong R P, Sakinofsky I, Kennedy J L. Genetic Factors and Suicidal Behavior. 2012.
4. Roy A, Segal N L, Sarchiapone M. Attempted suicide among living co-twins of twin suicide victims. Am J Psychiatry 1995; 152(7): 1075-1076.
5. Statham D J, Heath A C, Madden P A, Bucholz K K, Bierut L, Dinwiddie S H, et al. Suicidal behaviour: an epidemiological and genetic study. Psychol Med 1998; 28(4): 839-855.
6. Voracek M, Loibl L M. Genetics of suicide: a systematic review of twin studies. Wien Klin Wochenschr 2007; 119(15-16): 463-475.
7. Hesselbrock V, Dick D, Hesselbrock M, Foroud T, Schuckit M, Edenberg H, et al. The search for genetic risk factors associated with suicidal behavior. Alcohol Clin Exp Res 2004; 28(5 Suppl): 70S-76S.
8. Zubenko G S, Maher B S, Hughes H B, 3rd, Zubenko W N, Scott Stiffler J, Marazita M L. Genome-wide linkage survey for genetic loci that affect the risk of suicide attempts in families with recurrent, early-onset, major depression. Am J Med Genet B Neuropsychiatr Genet 2004; 129B(1): 47-54.

9. Willour V L, Zandi P P, Badner J A, Steele J, Miao K, Lopez V, et al. Attempted suicide in bipolar disorder pedigrees: evidence for linkage to 2p12. Biol Psychiatry 2007; 61(5): 725-727.
10. Perlis R H, Huang J, Purcell S, Fava M, Rush A J, Sullivan P F, et al. Genome-wide association study of suicide attempts in mood disorder patients. Am J Psychiatry 2010; 167(12): 1499-1507.
11. Schosser A, Butler A W, Ising M, Perroud N, Uher R, Ng M Y, et al. Genomewide association scan of suicidal thoughts and behaviour in major depression. PLoS One 2011; 6(7): e20690.
12. Willour V L, Seifuddin F, Mahon P B, Jancic D, Pirooznia M, Steele J, et al. A genome-wide association study of attempted suicide. Mol Psychiatry 2012; 17(4): 433-444.
13. Scott L J, Muglia P, Kong X Q, Guan W, Flickinger M, Upmanyu R, et al. Genome-wide association and meta-analysis of bipolar disorder in individuals of European ancestry. Proc Natl Acad Sci USA 2009; 106(18): 7501-7506.
14. Purcell S, Neale B, Todd-Brown K, Thomas L, Ferreira M A, Bender D, et al. PLINK: a tool set for whole-genome association and population-based linkage analyses. Am J Hum Genet 2007; 81(3): 559-575.
15. Howie B, Fuchsberger C, Stephens M, Marchini J, Abecasis G R. Fast and accurate genotype imputation in genome-wide association studies through pre-phasing. Nat Genet 2012; 44(8): 955-959.
16. Delaneau O, Zagury J F, Marchini J. Improved whole-chromosome phasing for disease and population genetic studies. Nat Methods 2013; 10(1): 5-6.
17. Abecasis G R, Altshuler D, Auton A, Brooks L D, Durbin R M, Gibbs R A, et al. A map of human genome variation from population-scale sequencing. Nature 2010; 467 (7319): 1061-1073.
18. Inatani M, Haruta M, Honjo M, Oohira A, Kido N, Takahashi M, et al. Upregulated expression of N-syndecan, a transmembrane heparan sulfate proteoglycan, in differentiated neural stem cells. Brain Res 2001; 920(1-2): 217-221.
19. Hienola A, Tumova S, Kulesskiy E, Rauvala H. N-syndecan deficiency impairs neural migration in brain. J Cell Biol 2006; 174(4): 569-580.
20. Kaksonen M, Pavlov I, Voikar V, Lauri S E, Hienola A, Riekki R, et al. Syndecan-3-deficient mice exhibit enhanced LTP and impaired hippocampus-dependent memory. Mol Cell Neurosci 2002; 21(1): 158-172.
21. Wetzel C, Hu J, Riethmacher D, Benckendorff A, Harder L, Eilers A, et al. A stomatin-domain protein essential for touch sensation in the mouse. Nature 2007; 445(7124): 206-209.
22. McGowan P O, Sasaki A, D'Alessio A C, Dymov S, Labonte B, Szyf M, et al. Epigenetic regulation of the glucocorticoid receptor in human brain associates with childhood abuse. Nat Neurosci 2009; 12(3): 342-348.
23. Perroud N, Paoloni-Giacobino A, Prada P, Olie E, Salzmann A, Nicastro R, et al. Increased methylation of glucocorticoid receptor gene (NR3C1) in adults with a history of childhood maltreatment: a link with the severity and type of trauma. Transl Psychiatry 2011; 1: e59.
24. Hubler T R, Scammell J G. Intronic hormone response elements mediate regulation of FKBP5 by progestins and glucocorticoids. Cell Stress Chaperones 2004; 9(3): 243-252.
25. Magee J A, Chang L W, Stormo G D, Milbrandt J. Direct, androgen receptor-mediated regulation of the FKBP5 gene via a distal enhancer element. Endocrinology 2006; 147(1): 590-598.
26. Kripke D F, Nievergelt C M, Tranah G J, Murray S S, Rex K M, Grizas A P, et al. FMR1, circadian genes and depression: suggestive associations or false discovery? J Circadian Rhythms 2013; 11(1): 3.
27. Brouwer J R, Severijnen E, de Jong F H, Hessl D, Hagerman R J, Oostra B A, et al. Altered hypothalamus-pituitary-adrenal gland axis regulation in the expanded CGG-repeat mouse model for fragile X-associated tremor/ataxia syndrome. Psychoneuroendocrinology 2008; 33(6): 863-873.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of treating a subject at risk for suicide, the method comprising assaying a biological sample obtained from the subject to determine the subject's genotype at the polymorphic site in one or more genetic markers associated with suicide, at least one marker being defined by rs2491144 (SEQ ID NO:1), by subjecting the biological sample to an analysis comprising PCR analysis, sequencing, 5'exonuclease fluorescence assay, probe hybridization or a combination thereof, identifying the subject as at risk for suicide where the biological sample contains a G allele at a polymorphic site in rs2491144 defined as position 26 of SEQ ID NO:1 and administering to the subject identified as at risk for suicide one or more of an antipsychotic agent, a mood stabilizer, an antidepressant, an anticonvulsant, an anxiolytic, or a combination thereof, or treating the subject with one or more of transcranial magnetic stimulation and electroconvulsive therapy.

2. The method of claim 1, further comprising assaying the subject's genotype at the polymorphic site in one or more additional genetic markers in the biological sample from the subject, the one or more additional genetic markers being defined by the group consisting of rs9315639 (SEQ ID NO:2), rs11082138 (SEQ ID NO:3), rs11697517 (SEQ ID NO:4), and rs2186437 (SEQ ID NO:5), wherein the presence of any of: a C allele at a polymorphic site in marker rs9315639 defined as position 26 of SEQ ID NO:2, a C allele at a polymorphic site in marker rs11082138 defined as position 26 of SEQ ID NO:3, a T allele at a polymorphic site in marker rs11697517 defined as position 26 of SEQ ID NO:4, and a C allele at a polymorphic site in marker rs2186437 defined as position 26 of SEQ ID NO:5, identifies the subject as at increased risk for suicide.

3. The method of claim 1, wherein the biological sample is a sample from blood, saliva, spinal fluid, brain biopsy, cultured cells obtained from the subject, stool, urine, autopsy samples, or frozen sections taken for histological purposes.

4. The method of claim 1, wherein the subject is a subject diagnosed with a mental illness.

5. The method of claim 4, wherein the mental illness is selected from the group consisting of depression, schizophrenia, schizoaffective disorder, bipolar disorder, personality disorder, seasonal affective disorder, anxiety disorder, and post traumatic stress disorder.

6. The method of claim 1, wherein the subject exhibits one or more clinical symptoms of a mental illness.

7. The method of claim 6, wherein the subject exhibits one or more symptoms of a mental illness selected from the group consisting of depression, schizophrenia, schizoaffective disorder, bipolar disorder, personality disorder, seasonal affective disorder, anxiety disorder, and post traumatic stress disorder.

8. The method of claim 1, further comprising receiving, in a computer system, the subject's genotype for the one or more genetic markers.

9. The method of claim 8, wherein the subject's genotype is received directly from equipment used in determining the subject's genotype.

10. The method of claim 8, further comprising receiving, in the computer system, the subject's diagnosis.

11. The method of claim 8, further comprising a step of outputting an indication of that the subject is at increased risk for suicide.

12. The method of claim 11, wherein the indication is represented on a patient specific report.

13. The method of claim 2, wherein the method further comprises a step performed by a computer readable medium containing executable instructions that when executed cause one or a plurality of processors to receive a subject's genotype for one or more of the genetic markers.

* * * * *